United States Patent
Couade

(10) Patent No.: US 11,995,807 B2
(45) Date of Patent: May 28, 2024

(54) METHOD FOR ULTRASOUND DETERMINATION OF A CORRECTED IMAGE OF A MEDIUM, AND DEVICE FOR IMPLEMENTING THIS METHOD

(71) Applicant: SUPERSONIC IMAGINE, Aix en Provence (FR)

(72) Inventor: Mathieu Couade, Aix en Provence (FR)

(73) Assignee: SUPERSONIC IMAGINE, Aix en Provence (FR)

( * ) Notice: Subject to any disclaimer, the term of this patent is extended or adjusted under 35 U.S.C. 154(b) by 399 days.

(21) Appl. No.: 17/612,167

(22) PCT Filed: May 14, 2020

(86) PCT No.: PCT/FR2020/050807
§ 371 (c)(1),
(2) Date: Nov. 17, 2021

(87) PCT Pub. No.: WO2020/234530
PCT Pub. Date: Nov. 26, 2020

(65) Prior Publication Data
US 2022/0222787 A1    Jul. 14, 2022

(30) Foreign Application Priority Data
May 17, 2019  (FR) .................... 19 05212

(51) Int. Cl.
*G06T 5/80* (2024.01)
*A61B 8/08* (2006.01)
(Continued)

(52) U.S. Cl.
CPC .............. *G06T 5/80* (2024.01); *A61B 8/485* (2013.01); *G06T 3/20* (2013.01); *G06T 3/60* (2013.01);
(Continued)

(58) Field of Classification Search
CPC .... G06T 5/80; G06T 3/20; G06T 3/60; G06T 3/50; G06T 7/20
See application file for complete search history.

(56) References Cited

U.S. PATENT DOCUMENTS 6,270,459 B1 *  8/2001  Konofagou .......... A61B 5/0053
                                                    600/449
8,154,227 B1 *  4/2012  Young .................... A63H 30/04
                                                    318/268
(Continued)

FOREIGN PATENT DOCUMENTS

EP    2 535 004 A1    12/2012
EP    2740407         6/2014
(Continued)

OTHER PUBLICATIONS

PCT International Preliminary Report on Patentability in Application PCT/FR2020/050807, dated Nov. 16, 2021, 12 pages.
(Continued)

*Primary Examiner* — Kevin Ky
(74) *Attorney, Agent, or Firm* — Merchant and Gould, PC

(57) ABSTRACT

Method for ultrasound determination of a corrected image of a medium, the method comprising: determination of a temporal succession of images (Ik) of the medium, determination of the movement for each image of the medium, determination of a temporal succession of partial strain images ($I\Delta\varepsilon_k$) based on images of the medium, determination of corrected partial strain images ($I\Delta\varepsilon_k^*$) by compensation of said partial strain images ($I\Delta\varepsilon_k$) based on preceding movements, and determination of a corrected strain image ($I\varepsilon_k^*$) by summation of the preceding corrected partial strain images ($I\Delta\varepsilon_k^*$).

16 Claims, 4 Drawing Sheets

(51) Int. Cl.
  *G06T 3/20* (2006.01)
  *G06T 3/60* (2006.01)
  *G06T 5/50* (2006.01)
  *G06T 7/20* (2017.01)

(52) U.S. Cl.
  CPC ............... *G06T 5/50* (2013.01); *G06T 7/20* (2013.01); *G06T 2207/10132* (2013.01); *G06T 2207/30004* (2013.01)

(56) References Cited

U.S. PATENT DOCUMENTS

| | | | |
|---|---|---|---|
| 11,064,964 B2* | 7/2021 | Tolkowsky | A61B 5/021 |
| 11,170,519 B2* | 11/2021 | Ebata | A61B 8/5223 |
| 2003/0163043 A1* | 8/2003 | Heimdal | G01S 15/8981 600/437 |
| 2005/0252295 A1 | 11/2005 | Fink et al. | |
| 2009/0036775 A1* | 2/2009 | Ikuma | A61B 8/5238 600/443 |
| 2009/0234230 A1 | 9/2009 | Bercoff et al. | |
| 2010/0016724 A1 | 1/2010 | Arai et al. | |
| 2010/0174185 A1* | 7/2010 | Wang | A61B 8/0841 600/562 |
| 2010/0220901 A1 | 9/2010 | Matsumura | |
| 2013/0041477 A1* | 2/2013 | Sikdar | A61F 2/583 623/57 |
| 2013/0317361 A1 | 11/2013 | Tabaru et al. | |
| 2014/0121520 A1* | 5/2014 | Wang | A61B 8/403 600/444 |
| 2015/0146953 A1 | 5/2015 | Yoshitomo et al. | |
| 2018/0242954 A1* | 8/2018 | Miyachi | G01S 7/52042 |
| 2018/0324332 A1* | 11/2018 | Konttori | G02B 3/0037 |
| 2019/0357878 A1* | 11/2019 | Nemoto | G06T 7/223 |
| 2019/0377051 A1* | 12/2019 | Bacher | G16H 40/63 |
| 2022/0222787 A1* | 7/2022 | Couade | G06T 5/50 |

FOREIGN PATENT DOCUMENTS

| | | |
|---|---|---|
| JP | 2010-012098 A | 1/2010 |
| JP | 2011-224346 A | 11/2011 |
| JP | 2013-500752 A | 1/2013 |
| JP | 2013-183982 A | 9/2013 |
| JP | 2014-207933 A | 11/2014 |
| JP | 2015-100613 A | 6/2015 |
| JP | 2015-144623 A | 8/2015 |
| JP | 5819428 | 11/2015 |
| JP | 2017-079977 A | 5/2017 |
| JP | 2017-080043 A | 5/2017 |
| JP | 2017-153540 A | 9/2017 |
| WO | 2007/083745 | 7/2007 |
| WO | 2008/075740 | 6/2008 |
| WO | 2009/063691 | 5/2009 |
| WO | 2010/098233 | 9/2010 |
| WO | 2012/105152 | 8/2012 |
| WO | 2013/153857 | 10/2013 |
| WO | 2014/010367 | 1/2014 |

OTHER PUBLICATIONS

International Search Report and Written Opinion of the International Searching Authority for International Patent Application No. PCT/FR2020/050807 dated Oct. 5, 2020, 12 pages.

French Search Report for French Patent Application No. FR19 05212 dated Apr. 2, 2020, 2 pages.

Bernal, M. et al., "In Vivo Quantification of the Nonlinear Shear Modulus in Breast Lesions: Feasibility Study", IEEE Transactions on Ultrasonics, Ferroelectrics, and Frequency Control, 63(1): 101-109 (Jan. 2016).

Bouguet, J., "Pyramidal Implementation of the Lucas Kanade Feature Tracker Description of the algorithm", Intel Corporation, 1-9 (2000).

Chammings, F. et al., "Shear wave elastography of the breast: effect of manual compression for the differentiation of benign from malignant lesions", European Society of Radiology, 1-10 (2014).

Gennisson, J. et al., "Acoustoelasticity in soft solids: Assessment of the nonlinear shear modulus with the acoustic radiation force", J. Acoust. Soc. Am., 122(6): 3211-3219 (Dec. 2007).

Latorre-Ossa, H. et al., "Quantitative Imaging of Nonlinear Shear Modulus by Combining Static Elastography and Shear Wave Elastography", IEEE Transactions on Ultrasonics, Ferroelectrics, and Frequency Control, 59(4): 833-839 (Apr. 2012).

O'Donnell, M. et al., "Internal Displacement and Strain Imaging Using Ultrasonic Speckle Tracking", IEEE Transactions on Ultrasonics, Ferroelectrics, and Frequency Control, 41(3): 314-325 (May 1994).

Ophir, J. et al., "Elastography: A Quantitative Method for Imaging the Elasticity of Biological Tissues", Ultrasonic Imaging, 13: 111-134 (1991).

* cited by examiner $$\ell n(E) = \ell n(E_0) - \frac{A}{\frac{4}{3}E_0} \varepsilon$$

METHOD FOR ULTRASOUND DETERMINATION OF A CORRECTED IMAGE OF A MEDIUM, AND DEVICE FOR IMPLEMENTING THIS METHOD

This application is a National Stage Application of PCT/FR2020/050807, filed 14 May 2020, which claims benefit of French Patent Application Serial No. FR19 05212, filed 17 May 2019, and which applications are incorporated herein by reference. To the extent appropriate, a claim of priority is made to each of the above disclosed applications.

TECHNICAL FIELD

This disclosure relates to methods and devices for imaging with ultrasonic waves in order to provide images of a viscoelastic medium. In particular, the aim of the method is to correct the produced images by taking into account a variation in the pressure exerted by an ultrasound imaging probe on an external surface of the medium.

PRIOR ART

More particularly, this disclosure relates to an imaging method using ultrasonic waves to observe a diffusing viscoelastic medium which contains particles reflecting said ultrasonic compression waves.

The images corrected by the method can be of various types. For example, the images can be of the strain type or of the elasticity type.

Patent US 2005/252295 proposes an elasticity imaging technique in which an elastic shear wave is generated in the medium, and the propagation of this elastic shear wave is observed by recording a plurality of images of the medium. Images of at least one movement parameter of the medium (displacement, partial strain) are then determined, and a shear wave propagation parameter is deduced from the images, such as the shear wave speed, shear modulus, Young's modulus, shear elasticity, etc.

This last technique is widely used. However, the images of the movement parameter or the images of the shear wave propagation parameter have been found to be sensitive to the pressure exerted by the ultrasound imaging probe on the surface of the medium. But this probe pressure is exerted by the practitioner and can vary during an examination or from one examination to another. Indeed, the practitioner varies this external pressure in order to obtain the desired observation in the image concerned.

In addition, these images comprise strains related to variations in the external pressure exerted, which generates inaccuracies in their representation, in their reproducibility, and in their determination.

DISCLOSURE OF THE INVENTION

The object of this invention is to improve the imaging methods of this type, particularly in order to improve the images themselves.

To this end, this disclosure proposes a method for ultrasound determination of a corrected image of a medium, characterized in that:
determination of a temporal succession of images of the medium ($I_k$), k being an image index between 0 and N, and the first image of said succession being assumed to be without strain,
determination of the movement for each image of the medium of index k between 1 and N, the movement being between an image of the medium of index k ($I_k$) and the preceding image of the medium of index k-1 ($I_{k-1}$),
determination of a temporal succession of partial strain images ($I\Delta\varepsilon_k$), based on the image of the medium of index k ($I_k$) and the preceding image of the medium of index k-1 ($I_{k-1}$)
determination of corrected partial strain images ($I\Delta\varepsilon_k^*$), by compensation of said partial strain images ($I\Delta\varepsilon_k$) based on preceding movements, meaning the movements associated with the images of the medium having indices between 1 and k inclusive, and
determination of a corrected strain image ($I\varepsilon_k^*$) by summation of the corrected partial strain images ($I\Delta\varepsilon_k^*$) of indices between 1 and k inclusive.

With these arrangements, one can ensure that the produced image is corrected.

In various embodiments of the method according to this disclosure, recourse may optionally also be made to one or more of the following arrangements.

According to one aspect, determination of the movement at index k is carried out by:
determination of a field of displacement between an image of the medium and the preceding image of the medium,
determination of an image geometric transformation based on said field of displacement, said geometric transformation representing the field of displacement with fewer than ten parameters.

According to one aspect, the field of displacement is calculated by intercorrelation between an image of the medium and the preceding image of the medium, or by an algorithm for tracking sub-images between an image of the medium and the preceding image of the medium.

According to one aspect, the tracking algorithm is a Lucas-Kanade algorithm.

According to one aspect, the geometric transformation comprises at least one translation, or a translation and a homothety, or a translation, a homothety, and a rotation.

According to one aspect, the geometric transformation $T_k$ comprises a translation, a homothety, and a rotation, and the geometric transformation is put in matrix form such that:

$$T_k = \begin{bmatrix} Hx\cdot\cos\theta & -Hz\cdot\sin\theta & Tx \\ Hx\cdot\sin\theta & Hz\cdot\cos\theta & Tz \\ 0 & 0 & 1 \end{bmatrix}$$

with the following parameters of the geometric transformation $T_k$ in the image plane:
Tx, Ty translation coefficients,
Hx, Hz coefficient of homothety, and
$\theta$ angle of rotation of axis perpendicular to the image plane.

According to one aspect, parameters of the geometric transformation are obtained by median values of a population of parameters that are calculated based on groups of points in the field of displacement.

According to one aspect:
a group comprises between three and ten points in the field of displacement, and
the population is greater than one hundred groups.
According to one aspect, the method further comprises:
(e1) determination of an elasticity image of the medium, and (e2) determination of a corrected elasticity image, by compensation of said elasticity image based on the preceding movements, meaning the movements associated with the images of the medium having indices between 0 and k inclusive.

According to one aspect, the elasticity image produced in step (e1) is generated by the following sub-steps:

(e1.1) an excitation step during which a shear wave is generated in the medium, by causing at least one focused ultrasonic wave to be emitted, (e1.2) an observation step during which the propagation of the shear wave is observed by determining a temporal succession of intermediate images of the medium, j being an intermediate image index between 0 and M, (e1.3) a processing step during which the elasticity image is determined based on said intermediate images of the medium and based on a shear wave propagation model.

According to one aspect, the following are further carried out:

determination of a plurality of corrected strain images, determination of a plurality of corrected elasticity images, said corrected strain images and said elasticity images being temporally interlaced, and determination of an image of a nonlinearity parameter, based on the plurality of corrected strain images and the plurality of corrected elasticity images.

According to one aspect, the value of each pixel of the image of a nonlinearity parameter is determined by strain linear regression of pairs of values, the first value of each pair corresponding to the value of a same pixel of a corrected strain image among the plurality and the second value of the pair corresponding to the value of a same pixel of an elasticity image among the plurality, said corrected strain image among the plurality and said corrected elasticity image among the plurality being temporally successive or temporally close, and wherein the strain linear regression is established on the basis of the following relation between strain and elasticity:

$$\ln(E) = \ln(E_0) - \frac{A}{\frac{4}{3} \cdot E_0} \cdot \varepsilon$$

where

E is the Young's modulus of the pixel of the corrected elasticity image considered, $E_0$ is the Young's modulus of the pixel of the first corrected elasticity image, ln( ) is the natural logarithm function, ε is the strain of the pixel of the corrected strain image considered, and A is the nonlinearity parameter determined for said pixel by said strain linear regression.

According to one aspect, the following are further carried out:

determination of a temporal succession of partial stress images corrected by multiplication of the corrected partial strain image of index k and of the corrected elasticity image of index k, determination of a corrected stress image by summation of the corrected partial stress images having indices between 1 and k inclusive.

According to one aspect, the following are further carried out:

determination of a plurality of corrected stress images, determination of a plurality of corrected elasticity images, said corrected stress images and said elasticity images being temporally interlaced, and determination of an image of a nonlinearity parameter, based on the plurality of corrected stress images and the plurality of corrected elasticity images.

According to one aspect, the value of each pixel of the image of a nonlinearity parameter is determined by stress linear regression of pairs of values, the first value of each pair corresponding to the value of a same pixel of a corrected stress image among the plurality and the second value of the pair corresponding to the value of a same pixel of an elasticity image among the plurality, said corrected stress image among the plurality and said corrected elasticity image among the plurality being temporally successive or temporally close, and wherein the stress linear regression is established on the basis of the following relation between stress and elasticity:

$$E = E_0 - \frac{A}{\frac{4}{3} \cdot E_0} \cdot \varepsilon$$

where

E is the Young's modulus of the pixel of the corrected elasticity image considered, $E_0$ is the Young's modulus of the pixel of the first corrected elasticity image, σ is the stress of the pixel of the corrected strain image considered, and A is the nonlinearity parameter determined for said pixel by said regression.

This disclosure also relates to an imaging device comprising an ultrasound probe and a microcomputer which are suitable for implementing the method for ultrasound determination of a corrected image of a medium as mentioned above.

BRIEF DESCRIPTION OF DRAWINGS

Other features and advantages of this disclosure will be apparent from the following description of various embodiments, given as non-limiting examples, with reference to the accompanying drawings.

In the drawings.

In the various figures, provided as illustrations, the same reference numerals designate identical or similar elements.

DETAILED DESCRIPTION

Imaging Device 1

Figure 1:
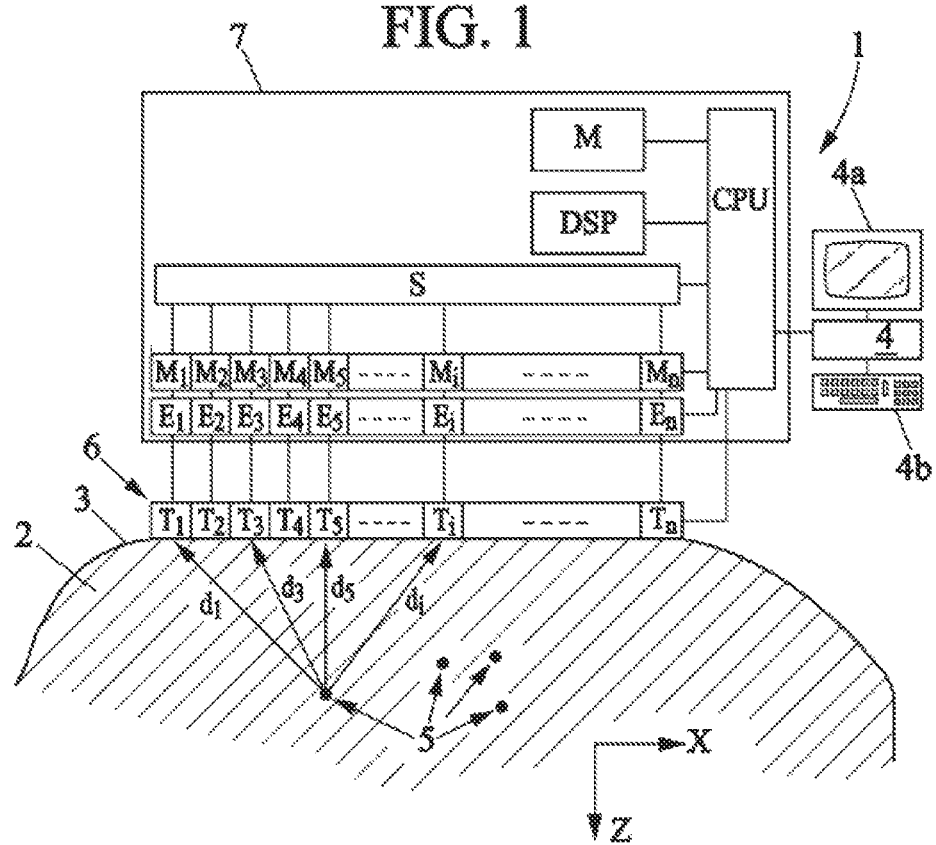
FIG. 1 is a schematic view of an ultrasound imaging device according to one embodiment of the disclosure.

The imaging device 1 shown in FIG. 1 is intended to provide images of a viscoelastic medium 2 which scatters the ultrasonic compression waves, and which for example can be a living body, for example part of a patient's body (breast, liver, abdomen, etc.) in the case of medical applications. This imaging device 1 is also suitable for studying the propagation of elastic shear waves in order to provide elasticity images of the medium 2.

The images of the medium are produced for example by means of a microcomputer 4 (comprising at least an input interface 4b such as a keyboard or the like, and an output interface 4a such as a screen or the like) or any other electronic processing unit, which sends into the medium 2, from its external surface 3, ultrasonic compression waves which interact with the scattering particles 5 contained in the medium 2, said particles being reflective to the ultrasonic compression waves. The particles 5 can be composed of any heterogeneity in the medium 2, and in particular, when a medical application is concerned, by collagen particles present in human tissues (these particles form dots on the ultrasound images known as "speckles").

To observe the medium 2 and generate images of the medium, an ultrasonic probe 6 placed against the external surface 3 of the observed medium 2 is used. This probe sends, along a Z axis, pulses of ultrasonic compression waves of the type commonly used in ultrasound, at a frequency for example of between 0.5 and 100 MHz and preferably between 0.5 and 15 MHz, for example about 4 MHz.

The ultrasonic probe 6 consists of an array of n ultrasonic transducers T1, T2, . . . , Ti, . . . , Tn, n being an integer greater than or at least equal to 1.

This probe 6 may for example be in the form of a linear array which may for example comprise n=128 transducers aligned along an X axis perpendicular to the Z axis. The probe in question may also be a two-dimensional array (planar or not) of transducers.

The transducers T1, T2, . . . Tn can be controlled independently of each other by the microcomputer 4, possibly by means of a central processing unit CPU which is contained for example in an electronics cabinet 7 connected to the probe 6 by a flexible cable. The transducers T1-Tn can thus selectively emit:

either a "plane" ultrasonic compression wave (in this case a wave whose wavefront is rectilinear in the X,Z plane) or any other type of unfocused wave illuminating the entire field of view in the medium 2, for example a wave generated by causing random acoustic signals to be emitted by the various transducers T1-Tn, or an ultrasonic compression wave focused at one or more points in the medium 2.

Patent US 2009/234230 proposes a synthetic imaging technique using several unfocused compression waves, for example plane wave type waves of different angles, and which combines the return waves of these plane waves in order to obtain very quickly an image of the medium of improved quality.

Determination of Images of the Medium $I_k$

To generate an image of the medium (I), the imaging device performs the following steps for example:

(i1) the microcomputer 4 causes the probe 6 to emit at least one unfocused ultrasonic compression wave into the viscoelastic medium, (i2) the microcomputer 4 causes the probe 6 to detect and record in real time the acoustic signals received from the viscoelastic medium 2, comprising the echoes generated by the unfocused ultrasonic compression wave by interacting with the reflecting particles 5 of the viscoelastic medium, and (i3) a processing step during which the microcomputer processes the acoustic signals received from the viscoelastic medium 2 during sub-step (i2), in order to determine one or more images of the medium (I).

The unfocused ultrasonic compression wave propagates in the medium 2 with a very high propagation speed, for example about 1500 m/s in the human body, and interacts with the reflecting particles 5, which generates echoes or other similar interference in the signal, these being known per se in the field of ultrasound by the name "speckle noise". Such "speckle noise" is captured by the transducers T1, . . . , Tn during sub-step (i2), after emitting an unfocused ultrasonic compression wave. The signal $si(t)$ thus captured by each transducer Ti is firstly sampled at high frequency (for example from 30 to 100 MHz) and digitized in real time by a sampler that is part of the cabinet 7 and connected to this transducer, respectively E1, E2, . . . En.

The signal $si(t)$ thus sampled and digitized is then stored, also in real time, in a memory Mi that is part of the cabinet 7 and specific to the transducer Ti.

Each memory Mi has, for example, a capacity of about 128 MB, and contains all the signals $si(t)$ received.

After storing all the signals $si(t)$, the central processing unit CPU causes these signals to be reprocessed by an adder circuit S that is part of the cabinet 7 (or it carries out this processing itself, or else said processing can be carried out in the microcomputer 4), by a conventional beamforming process corresponding to sub-step (i3).

Signals $S(x,z)$ are thus generated, these signals each corresponding to the image of the field of view of the medium after the firing of the unfocused ultrasonic wave.

For example, a signal $S(t)$ can be determined by the following formula:

$$S(x, z, t) = \sum_{i=1}^{n} \alpha_i(x, z) \cdot si[t(x, z) + d_i(x, z)/V]$$

in which:

$si$ is the raw signal perceived by transducer no. i after the firing of the ultrasonic compression wave, $t(x,z)$ is the time taken by the ultrasonic compression wave to reach the point at coordinates $(x,z)$ in the field of view, with $t=0$ when the emission begins, $d_i(x,z)$ is the distance between the point at coordinates $(x,z)$ in the field of view and transducer no. i, or an approximation of this distance, V is the average propagation speed of the ultrasonic acoustic compression waves in the observed viscoelastic medium, and αi(x,z) is a weighting coefficient incorporating apodization laws (in practice, in many cases it can be considered that αi(x,z)=1).

The above formula applies, mutatis mutandis, when the field of view is 3-dimensional (two-dimensional array of transducers), by replacing the spatial coordinates of the plane (x,z) by spatial coordinates (x,y,z).

After the optional beamforming step, the central processing unit CPU stores, in a central memory M that is part of the cabinet 7, the image signals S(x,z) corresponding to the last firing. These signals can also be stored in the microcomputer 4 so that it itself performs the calculation of the image of the medium (I).

Other techniques exist for generating an image of the medium (I), such as synthetic imaging techniques. Any imaging technique which allows obtaining images of the medium can be used. Preferably, a technique will be used which allows obtaining images at a high rate.

The imaging device 1 and the method according to this disclosure obtain a temporal succession of images of the medium in order to track the variation of the external pressure P exerted on the external surface 3. Thus, we will consider that a number N+1 of images of the medium are captured at successive time instants, these time instants not necessarily being separated by a constant period. The images of the medium can therefore be identified by an image index k between 0 and N.

The images of the medium will therefore be identified by the notation $I_k$.

This index k will be used for any other image or quantity determined based on the image of the medium of index k and possibly preceding images of the medium. This index can therefore be used to locate the time instant associated with this image of the medium of index k.

In addition, by convention, the first image of this succession of images is denoted as the image of the medium of index 0. It will be assumed that, for this first image, the external pressure P is low or zero, and that the induced strain on the external surface 3 is low or zero. This first image is for example represented in FIG. 2A.

Figure 2A:
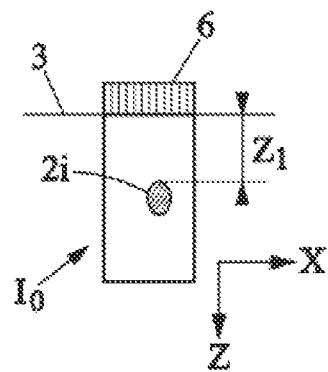
FIGS. 2A and 2B schematically represent the movement of an image of the medium between zero external pressure and an external pressure which deforms the external surface of the medium.
Figure 2B:
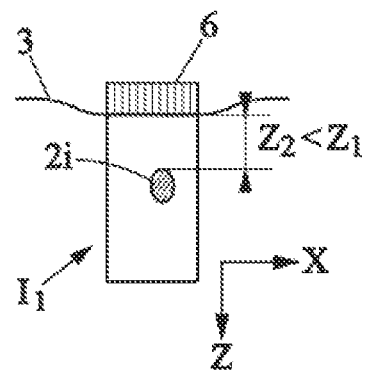
Figure 2C:
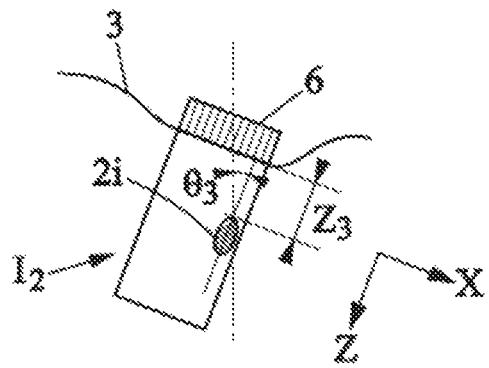
FIG. 2C schematically represents a more complex movement than that of FIG. 2B, this movement including a rotation.

FIGS. 2A to 2C illustrate the problem solved by this disclosure.

In FIG. 2A a use of the imaging device 1 is represented, the probe 6 exerting low or zero external pressure P on the external surface 3. The external surface 3 remains substantially horizontal (in the X direction). The image of the medium $I_0$ comprises, for example, an inclusion 2i at a depth Z1 relative to the external surface 3.

In FIG. 2B a use of the imaging device 1 at a time later than that of FIG. 2A is represented, and with an external pressure P' greater than P, which deforms the external surface 3 inwardly in direction Z within the medium 2. The imaging device 1 produces an image $I_1$ of the medium of the same size as the image $I_0$ produced in FIG. 2A, but the upper layers of the medium above the inclusion 2i are naturally more compressed than the lower layers of the medium 2 below the inclusion 2i, such that the inclusion 2i in this image $I_1$ of the medium of FIG. 2B is displaced towards the probe 6 in comparison with the first image $I_0$ of FIG. 2A. In other words, the inclusion 2i is then at a depth Z2 relative to the external surface 3 that is less than the depth Z1 of the first image I0.

Therefore, during a variation in the external pressure, the internal elements of the medium are displaced within the image of the medium because of the elasticity of said medium 2. It is thus necessary to know these general movements in order to perform a precise tracking and analysis of characteristics of these internal elements.

The example of FIGS. 2A and 2B shows that a translation in the Z direction could give an adequate correction.

In FIG. 2C, a use of the imaging device 1 at another time instant is shown, for example subsequent to the previous time instants shown in FIGS. 2A and 2B, and with a different external pressure P, and above all a tilting of the probe 6 relative to the vertical direction Z (the tilting is exaggerated in this FIG. 2C). The external surface 3 is deformed in the Z direction and is tilted at an angle Θ. The imaging device 1 produces an image of the medium $I_2$ of the same size, but the upper layers of the medium are also compressed and the inclusion 2i is displaced laterally in the image, i.e. displaced in the X direction by the tilting of the probe 6.

Thus, the variations in pressure and position of the probe 6 on the external surface 3 displace the internal elements of the medium within the image of the medium, and it appears necessary to know these general movements (very slow compared to the ultrasonic waves) in order to track and/or compensate for them in the captured images of the medium so as to perform an accurate analysis of characteristics of the internal elements.

The probe 6 may possibly have a more complex movement than a simple translation in the Z direction or a combination of a translation and a rotation. The necessary corrective movement will then be more complex. The details of determining these movements will be explained further below in this disclosure.

Determination of a Field of Displacement $u_k$

The images of the medium ($I_k$) can be processed by correlation and advantageously by intercorrelation, either two by two, i.e. between an image of the medium of index k ($I_k$) and the image of the medium of index k-1 ($I_{k-1}$).

The intercorrelation may be carried out for example in a specialized electronic circuit DSP that is part of the cabinet 7, or may be programmed in the central processing unit CPU or in the microcomputer 4.

During this intercorrelation process, an intercorrelation function $<S_{k-1}(x,z),S_k(x,z)>$ is maximized in order to determine the displacement undergone by each particle 5 giving rise to an ultrasonic echo.

Examples of such intercorrelation calculations are given in the state of the art, in particular in the following documents:

"*Internal displacement and strain imaging using speckle tracking*", O'Donnell et al, IEEE transactions on ultrasonic, ferroelectrics, and frequency control, vol. 41, no. 3, May 1994, p. 314-325, "*Elastography: a quantitative method for imaging the elasticity of biological tissues*", Ophir et al., Ultrasound imaging, Vol. 13, p.111-134, 1991, and "*Pyramidal Implementation of the Lucas Kanade Feature Tracker. Description of the algorithm.*", J-Y Bouguet, Intel Corp.

We thus obtain a field of displacement, i.e. a set of displacement vectors or u(x,z,t) at each position (x,z) of the medium 2, which we can denote $u_k(x,z)$ by replacing the variable of the time instant t by the image index k. These displacement vectors can optionally be reduced to a single component or to two or three components. In the example considered, the field of displacement $u_k$ at image index k is:

$$u = \begin{bmatrix} u_x \\ u_z \end{bmatrix}$$

This field of displacement (set of displacement vectors) is stored in the memory M or in the microcomputer 4.

An image of the field of displacement Iu$_k$ can be constructed, and the set of images of the field of displacement Iu$_k$ corresponding to the temporal succession of the images of the medium can be viewed, in particular by means of the screen 4a of the microcomputer, for example, in the form of a slow-motion film where the value of the displacements is illustrated by an optical parameter such as gray scale or chromatic scale.

Determination of Partial Strain Images IΔε$_k$

One can then calculate the partial strains Δε at each point of the medium 2, i.e. vectors whose components are derivatives of the components of the displacement vectors respectively relative to the spatial variables (X,Z coordinates in the example considered), i.e.:

$$\Delta \varepsilon = \begin{bmatrix} \frac{du_x}{dx} \\ \frac{du_z}{dz} \end{bmatrix}$$

Optionally, according to one exemplary implementation, only the strain/partial strain uniaxially in the Z direction is calculated. Indeed, the compression related to external pressure of the probe is mainly in this direction. In the same manner, in a subsequent stress calculation, only the stress/partial stress uniaxially in the Z direction is optionally calculated. The calculations are thus simplified.

As is true for the displacement vectors, a partial strain image (IΔε$_k$) can be constructed from the set of partial strains calculated at any point of coordinates (x,z) in the X-Z plane (image plane).

These partial strain vectors or partial strain images (IΔε$_k$) can be viewed, in particular by means of the screen 4a of the microcomputer, in the form of a slow-motion film.

Determination of Movement of the Medium by External Pressure

The strain of the medium 2 linked to variations in the external pressure P exerted on the external surface 3 is a slow, almost uniform elastic strain. This strain propagates inside the viscoelastic medium 2, and causes displacement of the particles 5 and of the elements included in the medium 2.

This displacement is detrimental to the analysis of characteristics of the various points of the image of the medium, and in particular to evaluating the strain at these points and/or the elasticity of these points.

This disclosure therefore considers correcting images to compensate for these movements, which makes it possible to maintain the particles and/or internal elements of the medium 2 at almost constant locations in the image, thus making it possible to study their characteristics more precisely.

The external strain caused by external pressure P can be considered as causing a movement between an image of the medium of index k (I$_k$) and a preceding image of the medium of index k-1 (I$_{k-1}$).

The movement can then be determined by the field of displacement (u$_k$) between an image of the medium of index k and a preceding image of the medium of index k-1.

In particular, this movement can be modeled by a geometric transformation T$_k$ of index k which represents, in a general and simple manner, all displacements of the field of displacement in the step of image index k, u$_k$(x,z), i.e. with a very small number of parameters, for example less than ten.

Then, a compensation for any type of images based on the preceding movements can be carried out by applying the above geometric transformations, i.e. by applying geometric transformations T$_i$, the index i varying from 1 to k.

According to a first variant, the geometric transformation T$_k$ comprises a translation, as shown between FIG. 2A and FIG. 2B.

According to a second variant, the geometric transformation T$_k$ comprises a translation and a homothety.

According to a second variant, the geometric transformation T$_k$ comprises a translation, a homothety, and a rotation.

Thus, in the X-Z plane (the image plane), the geometric transformation can be put in a matrix form of the following type:

$$T_k = \begin{bmatrix} Hx \cdot \cos\theta & -Hz \cdot \sin\theta & Tx \\ Hx \cdot \sin\theta & Hz \cdot \cos\theta & Tz \\ 0 & 0 & 1 \end{bmatrix}$$

with the following parameters for the geometric transformation (Tk):

Tx, Ty coefficients of translation in the image plane,

Hx, Hz coefficient of homothety in the image plane, and

θ angle of rotation of axis perpendicular to the image plane.

Thus, if we take three points P1, P2, and P3 of the image, with the respective coordinates (x1,z1), (x2,z2), (x3,z3), we have the following relations:

$$A = \begin{bmatrix} x1 & x2 & x3 \\ z1 & z2 & z3 \\ 1 & 1 & 1 \end{bmatrix}$$

$$B = \begin{bmatrix} x1+dx1 & x2+dx2 & x3+dx3 \\ z1+dz1 & z2+dz2 & z3+dz3 \\ 0 & 0 & 0 \end{bmatrix}$$

$$dx1 = u_{x1} \quad dx1 = u_{z1}$$
$$dx2 = u_{x2} \quad dz2 = u_{z2}$$
$$dx3 = u_{x3} \quad dz3 = u_{z3}$$

to reincorporate the notation of components X and Z of the displacement vectors of points P1, P2, and P3.

In addition, we have a relation making it possible to calculate the geometric transformation T$_k$ based on the above matrices A and B, i.e. a matrix A corresponding to the coordinates of the three points in the image, and a matrix B corresponding to the coordinates of these same three points with the displacements of these points (the movement). Thus, the matrix of the geometric transformation is obtained by the matrix product of matrix B and the inverse of matrix A:

$$T_k = B \cdot A^{-1}$$

Applying this relation allows us to calculate the geometric transformation T$_k$ from three points P1, P2, P3.

Conversely, once the geometric transformation T$_k$ has been established, this relation makes it possible to know the coordinates (x,z) of any point P by the inverse relation:

$$B = T_k \cdot A$$

A compensation can then be carried out for any type of images based on the preceding movements, by matrix multiplication of the preceding geometric transformations, i.e. by matrix multiplication of the geometric transformations $T_i$, the index i varying from 1 to k.

The above relations established with 3 points can be generalized to a group of points of the image, the group of points comprising 3, 4, 5, or 6 points of the image. The group of points consists of between three and ten points of the image.

In addition, in a variant, a population of three points (of a group of points) of the image is advantageously taken, said population comprising a number Ng of groups of points of high value. For example, the size of this population, the number Ng of groups of points is greater than one hundred.

Then, the parameters of the geometric transformation $T_k$ are obtained by median values of the parameters calculated from the population of groups of points of the image.

In particular, this technique can be applied to an image of the field of displacement $u_k$ in order to deduce the movement between an image of the medium of index k and a preceding image of the medium of index k-1.

By using a population of groups of points, one can determine a geometric transformation that more generally represents the movement between the image of the medium of index k and a preceding image of the medium of index k-1.

Advantageously, the selection of points in each group is made randomly in the image. Due to this arrangement, it is possible to determine a geometric transformation which represents the movement between images more generally and in a more reliable manner.

Determination of Corrected Partial Strain Images $I\Delta\varepsilon_k^*$

The partial strain images $I\Delta\varepsilon_k$ are then corrected in order to return these images to a situation in accordance with the first image of the medium $I_0$, thus eliminating the movements caused by strain from external pressure P in these partial strain images $I\Delta\varepsilon_k$.

This correction is carried out by using, for each partial strain image $I\Delta\varepsilon_k$ of image index k, the set of general movements determined between each image of the medium. More precisely, the reverse movements must be applied in order to return to the situation of the first image $I_0$.

In other words, the corrected partial strain images $I\Delta\varepsilon_k^*$ contain corrected partial strains $\Delta\varepsilon_k^*$ and they are calculated by compensation of said partial strain images $I\Delta\varepsilon_k$ based on movements associated with images of the medium having indices between 1 and k inclusive.

Determination of a Corrected Strain Image $I\varepsilon_k^*$

The strain $\varepsilon_k(x,z)$ is obtained by totaling the successive partial strains, i.e.:

$$\varepsilon_k(x, z) = \sum_{i=1}^{k} \Delta\varepsilon_i(x, z)$$

In the present case, the strain $\varepsilon_k(x,z)$ (corrected strain) is obtained by totaling the corrected successive partial strains $\Delta\varepsilon_k^*$:

$$\varepsilon_k^*(x, z) = \sum_{i=1}^{k} \Delta\varepsilon_i^*(x, z)$$

One can construct a corrected strain image ($I\Delta\varepsilon_k^*$) from the set of corrected strains $\varepsilon_k(x,z)$ calculated at any point having coordinates (x,z) in the XZ plane (image plane).

These corrected strain images $I\varepsilon_k^*$ can be viewed as a slow-motion movie.

Method for Determining a Corrected Image

Figure 3:
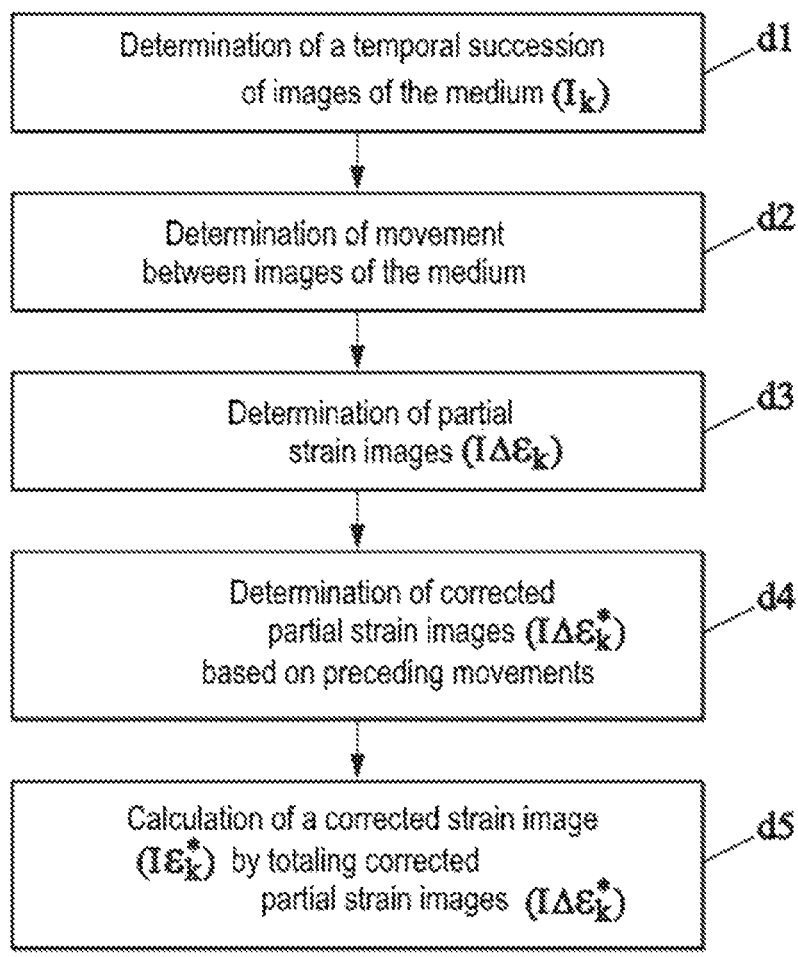
FIG. 3 is a diagram showing one embodiment of the method for calculating a corrected strain image.

In summary, according to a first embodiment of the method represented in FIG. 3 according to this disclosure, the method implemented comprises the following steps:

(d1) determination of a temporal succession of images of the medium ($I_k$), k being an image index between 0 and N, and the first image of said succession being assumed to be without strain, (d2) determination of the movement for each image of the medium of index k between 1 and N, the movement being between an image of the medium of index k ($I_k$) and the preceding image of the medium of index k-1 ($I_{k-1}$).

(d3) determination of a temporal succession of partial strain images ($I\Delta\varepsilon_k$), based on the image of the medium of index k ($I_k$) and the preceding image of the medium of index k-1 ($I_{k-1}$), (d4) determination of corrected partial strain images ($I\Delta\varepsilon_k^*$), by compensation of said partial strain images ($I\Delta\varepsilon_k$) based on the preceding movements, i.e. the movements associated with the images of the medium having indices between 1 and k inclusive, (d5) determination of a corrected strain image ($I\varepsilon_n^*$), by a summation or totaling of the corrected partial strain images ($I\Delta\varepsilon_n^*$) of indices between 1 and k inclusive.

Summation or totaling of images is understood to mean that the values of pixels having the same spatial coordinates in said images are summed (i.e. added together) to form the value of the corresponding pixel in the resulting image.

With these arrangements, a corrected strain image $I\varepsilon_n^*$ of the medium 2 is obtained which is not or is only slightly influenced by the deformations and movements induced by external pressure P, which makes it possible to obtain more accurate and more precise strain values than in the prior art.

Determination of an Elasticity Image of the Medium $IE_k$

Patent US 2005/252295 proposes a technique for imaging the elasticity of the viscoelastic medium 2: The imaging device 1 studies the propagation of elastic shear waves in this medium. The movements of the elastic shear waves are tracked by the means described above, and in particular by the microcomputer 4.

This is performed in several steps:

(e1.1) an excitation step during which the microcomputer 4 causes an elastic shear wave to be generated in the viscoelastic medium 2, by causing at least one ultrasonic wave focused in the viscoelastic medium to be emitted by the probe 6, (e1.2) an observation step during which the propagation of the shear wave is observed simultaneously at a multitude of points in the field of view in the viscoelastic medium 2, this step comprising sub-steps during which a plurality of temporally successive intermediate images of the medium are generated, j being an intermediate image index between 0 and M inclusive, M+1 being the number of intermediate images produced.

Each intermediate image of the medium is for example generated by the method for determining an image of the medium $I_k$ described above, in which at least one firing of an unfocused ultrasonic compression wave is emitted by the probe 6, and the received acoustic signals are detected and recorded by the probe 6, and these acoustic signals are processed in order to construct an intermediate image of the medium ($II_{j,k}$).

The focus and timing of the focused ultrasonic wave emitted in step (e1), as well as the timing of the unfocused ultrasonic waves emitted in step (e2), are adapted so that unfocused ultrasonic waves arrive in the field of view during the propagation of the shear wave in this field of view. Thus, the shear wave is visible in the generated intermediate images of the medium ($II_{j,k}$).

One then proceeds with:
(e1.3) a step of processing intermediate images of the medium in order to determine an elasticity image of the medium $IE_k$.

The intermediate images of the medium $II_{j,k}$ are processed to calculate a field of displacement $u_{j,k}$, for example by correlation or intercorrelation as above. As an example, by intercorrelation between an intermediate image of the medium of index j ($II_{j,k}$) and the intermediate image of the medium of index j-1 The determined displacement vectors can be used to visualize the propagation of the shear wave in the form of a movie. Optionally, one can further compute the partial strains $\Delta\varepsilon$ at each point of the medium 2, based on the field of displacement.

Based on the fields of displacements or strains, the microcomputer 4 can advantageously then proceed to a mapping step during which, based on the evolution of the movement parameter (displacement or partial strain) over time in the field of view, at least one propagation parameter of the shear wave is calculated, either at certain points of the chosen field of view, or throughout the entire field of view.

We can then construct an elasticity image $IE_k$, corresponding to the set of shear wave propagation parameters at various points in the field of view.

This elasticity image $IE_k$ of the medium can be viewed, in particular by means of the screen 4a of the microcomputer where the value of the propagation parameter is illustrated by an optical parameter such as a gray scale or a chromatic scale.

The shear wave propagation parameter which is calculated during the mapping step is chosen for example among:
the speed Cs of the shear waves, or
the shear modulus μ, or
the Young's modulus E=3μ, or
the attenuation α of the shear waves, or
the shear elasticity μ1, or
the shear viscosity μ2, or
the mechanical relaxation time TS of the tissues of the medium.

For example, the following can be calculated at different points in the field of view:
the value of the velocity Cs of the shear wave, which gives access to the hardness of the tissues,
the value of the mechanical relaxation time TS of the tissues, characteristic of the local viscosity of the medium.

For this purpose, we use a shear wave propagation model, for example represented by the following propagation equation, obeyed by the displacements u generated by the shear waves at each position r of the medium:

$$\rho \frac{\partial^2 \vec{u}(\vec{r}, t)}{\partial t^2} = c_s^2 \left(1 + \tau_s \frac{\partial \cdot}{\partial t}\right) \cdot \vec{\nabla}^2 \vec{u}(\vec{r}, t)$$

where
ρ is the density of the tissues,
τS is the mechanical relaxation time of the tissues, and
cS is the velocity of the shear wave, directly related to the Young's modulus E of the tissues by the relation:

$$c_s = \sqrt{\frac{E}{3\rho}}$$

Solving this propagation equation with the set of displacements u makes it possible to obtain the propagation parameters (cS, τS) mentioned above.

Variants in calculating the propagation parameter(s) are possible. In particular, the wave equation can be used in the Fourier domain, for example by averaging the values over a frequency band. One can also use partial strains instead of displacements.

One can also establish maps of propagation parameters, i.e. elasticity images, with different shear waves. It is then possible to combine them, for example by averaging them, to obtain a more precise mapping.

The propagation speed of the shear wave in the medium is sufficiently large to consider that there is no variation in the external pressure P exerted on the external surface 3 during this process during which a plurality of images of the medium are captured (intermediate images) intended for determining an elasticity image IE (shear wave propagation parameter). Thus, these images of the medium are not corrected for movements of the medium.

On the other hand, the elasticity image of the medium $IE_k$ must be corrected for movement at the time instant considered or at a close time instant (represented by the index k) in order to allow comparison with the initial image of the medium $I_0$ or comparison with the corrected strain image $I\varepsilon_k^*$.

Determination of a Corrected Elasticity Image $IE_k^*$

Figure 4:
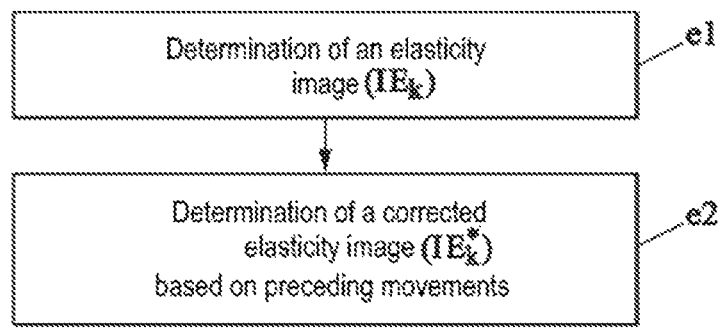
FIG. 4 is a diagram showing a method for determining a corrected elasticity image.

The elasticity image $IE_k$ is then corrected in a method represented in FIG. 4, where the goal is to return this elasticity image $IE_k$ to a situation in accordance with the first image of the medium $I_0$ in order to eliminate the movements caused by strain from external pressure P.

This correction is carried out by using, for each elasticity image $IE_k$ of image index k, the set of general movements determined between each image of the medium. More specifically, the reverse movements must be applied in order to return to the situation of the first image $I_0$.

In other words, the method comprises the following steps:
(e1) determination of an elasticity image (IEk),
(e2) determination of a corrected elasticity image ($IE_k^*$), by compensation of the elasticity image ($IE_k$) based on preceding movements associated with the images of the medium having indices between 1 and k inclusive.

Determination of an Image of a Nonlinearity Parameter $INL_k$

In a linear elastic domain, the medium 2 is deformed proportionally to the stress a and follows Hooke's law:

$$\sigma = E_0 \cdot \varepsilon$$

where
$E_0$ is the Young's modulus of the linear domain, and
ε is the strain.

In a non-linear elastic domain, this proportionality is no longer valid. In most cases, the Young's modulus E of the material of the medium 2 increases with compression.

We then define the modulus of elasticity or Young's modulus E as being the slope of the stress-strain curve, i.e.:

$$E = \frac{\Delta\sigma}{\Delta\varepsilon} \quad \text{(eq. 1)}$$

where
E is Young's modulus,
$\Delta\sigma$ is the local stress variation, i.e. the partial stress,
$\Delta\varepsilon$ is the local strain variation, i.e. the partial strain.

A nonlinearity parameter of the elasticity can for example be the Landau coefficient called the third order elastic modulus A mentioned in the following documents:

"*Acoustoelasticity in soft solids: Assessment of the nonlinear shear modulus with the acoustic radiation force*", Gennisson et Al., J. Acoust. Soc. Am (122), December 2007, p. 3211 3219, and "*Quantitative Imaging of Nonlinear Shear Modulus by Combining Static Elastography and Shear Wave Elastography*", H. Latorre-Ossa et al., IEEE Transactions on Ultrasonics, Ferroelectrics, and Frequency Control, Vol. 51, no. 4, p. 833-839.

In particular, equation (1) of the latter document can be rewritten in the form of a relation (R1) between the elasticity (Young's modulus) E and the stress $\sigma$:

$$E = E_0 - \frac{A}{\frac{4}{3} \cdot E_0} \cdot \sigma \quad \text{(eq. 2)}$$

where
E is the Young's modulus or modulus of elasticity,
$E_0$ is the Young's modulus of the linear domain, i.e. the Young's modulus of the material of the medium without compression, therefore the first corrected elasticity image in the temporal succession of the images,
$\sigma$ is the stress and for example the uniaxial stress $\sigma_z$ in the Z direction (vertical), substantially corresponding to the compression induced by the external pressure exerted by the user of the probe 6, and
A is the nonlinearity parameter desired.

By differentiating the previous relation R1, we obtain:

$$\Delta E = -\frac{A}{\frac{4}{3} \cdot E_0} \cdot \Delta\sigma$$

By dividing by the definition of the Young's modulus from equation (eq. 1) and by integration we obtain a relation R2 between the elasticity (Young's modulus) E and the strain $\varepsilon$, which is:

$$\ln(E) = \ln(E_0) - \frac{A}{\frac{4}{3} \cdot E_0} \cdot \varepsilon \quad \text{(eq. 3)}$$

where
E is the Young's modulus,
$E_0$ is the Young's modulus of the linear domain, i.e. the Young's modulus of the material of the medium without compression, therefore the first corrected elasticity image in the temporal succession of the images,
ln( ) is the natural logarithm function,
$\varepsilon$ is the strain, and
A is the nonlinearity parameter to be determined.

Figure 5:
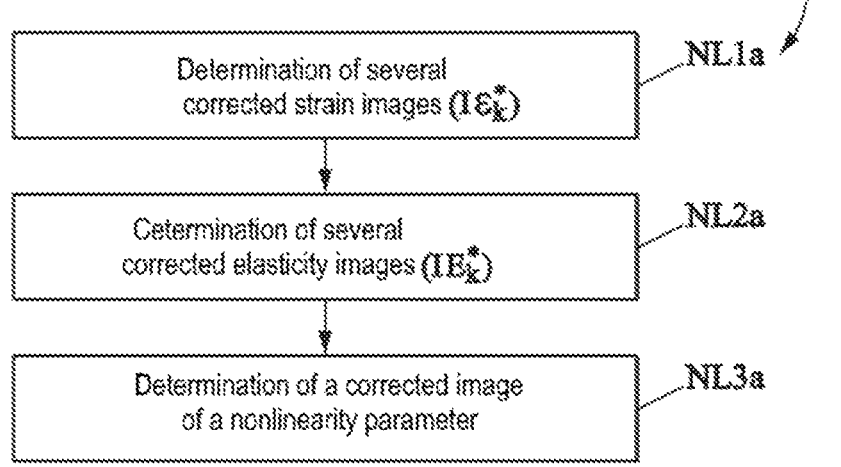
FIG. 5 is a diagram showing a first embodiment of a method for determining an image of a corrected nonlinearity parameter.

According to a first variant of the method NLa, represented in FIG. 5, based on strain images and elasticity images, the method implemented by the microcomputer 4 further comprises the following steps:

(NL1a) determination of a plurality of corrected strain images ($I\varepsilon_k^*$), as presented above, (NL2a) determination of a plurality of corrected elasticity images ($IE_k^*$), as presented above, said corrected strain images and said elasticity images being temporally interlaced, and (NL3a) determination of an image of a nonlinearity parameter ($INL_k$), based on the plurality of corrected strain images ($I\varepsilon_k^*$) and the plurality of corrected elasticity images ($IE_k^*$).

In fact, a nonlinearity parameter of a pixel in the image is determined by the set (the plurality) of corrected strain and corrected elasticity values for that pixel.

For example, this nonlinearity parameter is determined by linear regression of this plurality of pairs of values. We will call this linear regression a strain linear regression.

Each pair of values is formed for a pixel of the image, and comprises:
a first value of this same pixel from a corrected strain image, and
a second value of this same pixel from a corrected elasticity image,
the corrected strain and elasticity images concerned being temporally successive or temporally close images. These images may have the same or similar image indices.

Optionally, the strain images and the elasticity images can have different image indices and it is necessary to take images having indices corresponding to temporally successive or temporally close instants as explained above, i.e. a correspondence is made between the time and the index of each image considered.

Figure 6:
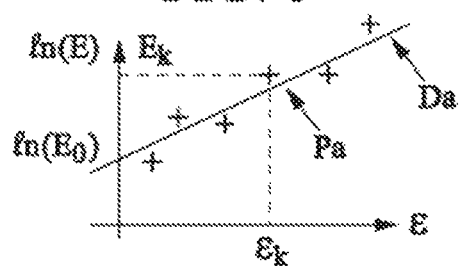
FIG. 6 is a graph showing an example implementation of the method of FIG. 5.

FIG. 6 is a representation of a plurality of points Pa for an image pixel, each point Pa corresponding to such a pair of values ($E_k$, $\varepsilon_k$). All these points Pa are substantially aligned along a straight line Da in a graph having the corrected strain value $\varepsilon$ (for this pixel) for the abscissa and having the natural logarithm of the value of the Young's modulus E (for this same pixel of the image) for the ordinate.

The strain linear regression then uses relation R2 between the elasticity (Young's modulus) E and the strain 8 (eq. 3):

$$\ln(E) = \ln(E_0) - \frac{A}{\frac{4}{3} \cdot E_0} \cdot \varepsilon$$

where, more specifically in the present case:
E is the Young's modulus of the pixel of the corrected elasticity image considered,
$E_0$ is the Young's modulus of the pixel of the first corrected elasticity image,
ln( ) is the natural logarithm function,
$\varepsilon$ is the strain of the pixel of the corrected strain image considered, and A is the nonlinearity parameter determined for said pixel by said strain linear regression.

The resolution of this strain linear regression for a set of pairs of values extracted from the plurality of corrected strain images ($I\varepsilon_k^*$) and corrected elasticity images ($IE_k^*$) gives the values of the nonlinearity parameter A for each pixel in the image.

By means of these calculations, we obtain an image of a nonlinearity parameter $INL_k$ of the medium 2 which uses corrected images. This image does not have the artifacts from uncorrected images of the prior art. This image is not or is only slightly influenced by the deformations and movements induced by external pressure P. More accurate and more precise nonlinearity parameter values A are obtained than with the methods of the prior art.

Figure 7A:
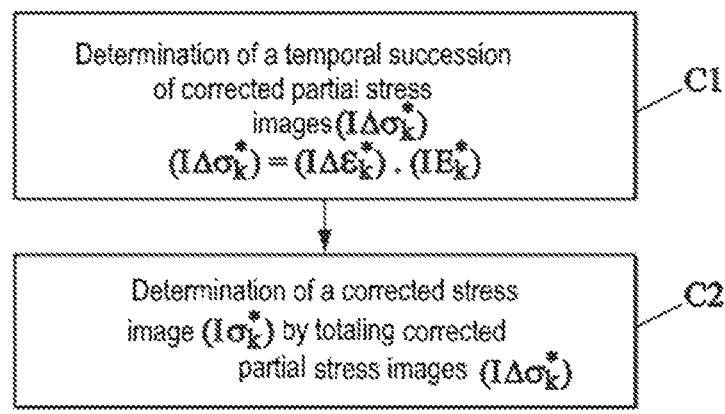
FIG. 7A is a diagram showing a method for determining a corrected stress image.
Figure 7B:
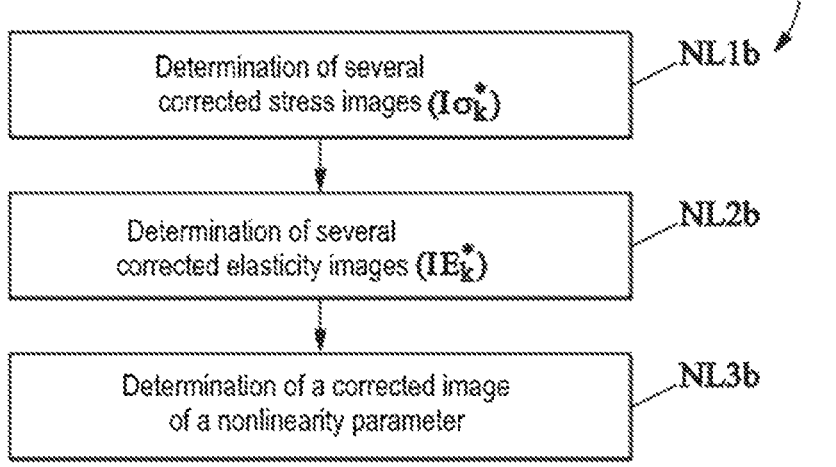
FIG. 7B is a diagram showing a second embodiment of a method for determining an image of a corrected nonlinearity parameter.

According to a second variant of the method NLb, represented in FIGS. 7A and 7B, based on stress images and elasticity images, the method implemented by the microcomputer 4 comprises:

a first phase during which partial strain images are converted into corrected stress images, and a second phase during which an image of a nonlinearity parameter is determined.

During the first phase, represented in FIG. 7A, the following is carried out:

(c1) determination of a temporal succession of corrected partial stress images ($I\Delta\sigma_k^*$) by multiplication of the corrected partial strain image ($I\Delta\varepsilon_k^*$) of index k and the corrected elasticity image ($IE_k^*$) of index k, and (c2) determination of a corrected stress image ($I\sigma_k^*$) by summation of the corrected partial stress images ($I\Delta\sigma_k^*$) having indices between 1 and k inclusive.

Multiplication of images is understood here to mean that the values of pixels having the same spatial coordinates in said images are multiplied (i.e. multiplied together) to form the value of the corresponding pixel of the resulting image. Here, we therefore multiply a corrected partial strain value $\Delta\varepsilon^*$, calculated by the steps of the method explained above and illustrated in FIG. 3, by a corrected elasticity value $E^*$ (corrected Young's modulus), calculated by the steps of the method explained above and illustrated in FIG. 4, to obtain the corrected stress value $\Delta\sigma^*$ for said pixel.

Thus, the partial stress is calculated at each pixel of the image by:

$$\Delta\sigma^* = E^* \cdot \Delta\varepsilon^*$$

Summation or totaling of images is understood to mean that the values of pixels having the same spatial coordinates in said images are summed (i.e. added together) to form the value of the corresponding pixel in the resulting image.

This means that:

$$\sigma_k^*(x, z) = \sum_{i=1}^{k} \Delta\sigma_i^*(x, z)$$

This formula is applied to any pixel of the image to construct the corrected stress image ($I\sigma_k^*$).

During the second phase represented in FIG. 7B, the following is carried out:

(NLb1) determination of a plurality of corrected stress images ($I\sigma_k^*$), (NLb2) determination of a plurality of corrected elasticity images ($IE_k^*$), said corrected stress images and said elasticity images being temporally interlaced, and (NLb3) determination of an image of a nonlinearity parameter ($INL_k$), based on the plurality of corrected stress images ($I\sigma_k^*$) and the plurality of corrected elasticity images ($IE_k^*$).

In fact, a nonlinearity parameter of a pixel in the image is determined by the set (the plurality) of corrected stress and corrected elasticity values for that pixel.

For example, this nonlinearity parameter is determined by linear regression of this plurality of pairs of values. We will call this linear regression a stress linear regression.

Each pair of values is formed for a pixel of the image, and comprises:

a first value of this same pixel of a corrected stress image, and a second value of this same pixel of a corrected elasticity image, the corrected stress and elasticity images concerned being temporally successive or temporally close images. These images can have the same or similar image indices.

Optionally, the stress images and the elasticity images can have different image indices and it is necessary to take images having indices corresponding to temporally successive or temporally close instants as explained above, i.e. a correspondence is made between the time and the index of each image considered.

Figure 8:
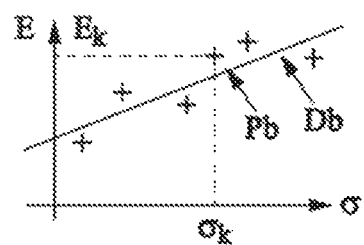
FIG. 8 is a graph showing an example implementation of the method of FIG. 7B.

FIG. 8 is a representation of a plurality of points Pb for an image pixel, each point Pb corresponding to a pair of values ($E_k$, $\sigma_k$). All these points Pb are substantially aligned along a straight line Db in a graph having the corrected stress value $\sigma$ (for this pixel) for the abscissa and having the value of the Young's modulus E (for this same pixel of the image) for the ordinate.

The stress linear regression then uses relation R1 between the elasticity (Young's modulus) E and the stress $\sigma$ (eq. 2):

$$E = E_0 - \frac{A}{\frac{4}{3} \cdot E_0} \cdot \sigma$$

where, more specifically in the present case:

E is the Young's modulus of the pixel of the corrected elasticity image considered, $E_0$ is the Young's modulus of the pixel of the first corrected elasticity image, $\sigma$ is the stress of the pixel of the corrected strain image considered, and A is the nonlinearity parameter determined for said pixel by said stress regression.

The resolution of this stress linear regression for a set of pairs of values extracted from pluralities of corrected stress images ($I\sigma_k^*$) and corrected elasticity images ($IE_k^*$) gives the values of the nonlinearity parameter A for each pixel in the image.

By means of these calculations, we obtain an image of a nonlinearity parameter $INL_k$ of the medium 2 which uses corrected images. This image does not have the artifacts from uncorrected images of the prior art. This image is not or is only slightly influenced by the deformations and movements induced by external pressure P. More accurate and more precise nonlinearity parameter values A are obtained than in the prior art.

The invention claimed is:

1. Method for ultrasound determination of a corrected image of a medium, the method comprising:
   determining a temporal succession of images of the medium ($I_k$), k being an image index between 0 and N, and the first image of said succession being assumed to be without strain,
   determining a movement for each image of the medium of index k between 1 and N, the movement being between an image of the medium of index k ($I_k$) and a preceding image of the medium of index k-1 ($I_{k-1}$),
   determining a temporal succession of partial strain images ($I\Delta\varepsilon_k$), based on the image of the medium of index k ($I_k$) and the preceding image of the medium of index k-1 ($I_{k-1}$),
   determining corrected partial strain images ($I\Delta\varepsilon_k^*$), by compensation of said partial strain images ($I\Delta\varepsilon_k$) based on preceding movements, wherein the movements associated with the images of the medium have indices between 1 and k inclusive, and
   determining a corrected strain image ($I\varepsilon_k^*$) by summation of the corrected partial strain images ($I\Delta\varepsilon_k^*$) of indices between 1 and k inclusive.

2. Method according to claim 1, wherein the determination of movement at index k comprises:
   determining a field of displacement ($u_k$) between the image of the medium ($I_k$) and the preceding image of the medium ($I_{k-1}$),
   determining an image geometric transformation ($T_k$) based on said field of displacement ($u_k$), said image geometric transformation representing the field of displacement ($u_k$) with fewer than ten parameters.

3. Method according to claim 2, wherein the field of displacement is calculated by intercorrelation between the image of the medium (Ik) and the preceding image of the medium (Ik-1), or by an algorithm for tracking sub-images between the image of the medium (Ik) and the preceding image of the medium (Ik-1).

4. Method according to claim 3, wherein the tracking algorithm is a Lucas-Kanade algorithm.

5. Method according to claim 2, wherein the geometric transformation (Tk) comprises at least one translation, or a translation and a homothety, or a translation, a homothety, and a rotation.

6. Method according to claim 2, wherein the geometric transformation (Tk) comprises a translation, a homothety, and a rotation, and wherein the geometric transformation is put in matrix form such that:

$$T_k = \begin{bmatrix} Hx.\cos\theta & -Hz.\sin\theta & Tx \\ Hx.\sin\theta & Hz.\cos\theta & Tz \\ 0 & 0 & 1 \end{bmatrix}$$

with the following parameters of the geometric transformation (Tk) in the image plane:
   Tx, Ty translation coefficients,
   Hx, Hz coefficient of homothety, and
   $\theta$ angle of rotation of axis perpendicular to the image plane.

7. Method according to claim 2, wherein the parameters of the geometric transformation (Tk) are obtained by median values of a population of parameters that are calculated based on groups of points in the field of displacement (uk).

8. Method according to claim 7, wherein:
   the at least one group of points comprises between three and ten points of the field of displacement ($u_k$), and
   the population is greater than one hundred groups of points.

9. Method according to claim 1, further comprising:
   (e1) determining determination of an elasticity image ($IE_k$) of the medium, and
   (e2) determining determination of a corrected elasticity image ($IE_k^*$), by compensation of said elasticity image ($IE_k$) based on the preceding movements, wherein the movements associated with the images of the medium have indices between 0 and k inclusive.

10. Method according to claim 9, wherein the elasticity image (IEk) is generated by:
    (e1.1) an excitation step during which a shear wave is generated in the medium, by causing at least one focused ultrasonic wave to be emitted,
    (e1.2) an observation step during which the propagation of the shear wave is observed by determining a temporal succession of intermediate images of the medium ($II_{j,k}$), j being an intermediate image index between 0 and M, and
    (e1.3) a processing step during which the elasticity image ($IE_k$) is determined based on said intermediate images of the medium ($II_{j,k}$) and based on a shear wave propagation model.

11. Method according to claim 9, further comprising:
    determining a plurality of corrected strain images ($I\varepsilon_k^*$),
    determining a plurality of corrected elasticity images ($IE_k^*$), said corrected strain images and said elasticity images being temporally interlaced, and
    determining an image of a nonlinearity parameter ($INL_k$), based on the plurality of corrected strain images ($I\varepsilon_k^*$) and the plurality of corrected elasticity images ($IE_k^*$).

12. Method according to claim 11, wherein the value of each pixel of the image of a nonlinearity parameter ($INL_k$) is determined by strain linear regression of pairs of values, the first value of each pair corresponding to the value of a same pixel of a corrected strain image among the plurality and the second value of the pair corresponding to the value of a same pixel of an elasticity image among the plurality, said corrected strain image among the plurality and said corrected elasticity image among the plurality being temporally successive or temporally close, and
    wherein the strain linear regression is established on the basis of the following relation between strain and elasticity:

$$\ln(E) = \ln(E_0) - \frac{A}{\frac{4}{3} \cdot E_0} \cdot \varepsilon$$

where
   E is the Young's modulus of the pixel of the corrected elasticity image considered,
   $E_0$ is the Young's modulus of the pixel of the first corrected elasticity image,
   ln( ) is the natural logarithm function,
   $\varepsilon$ is the strain of the pixel of the corrected strain image considered, and
   A is the nonlinearity parameter of said pixel, determined by said strain linear regression.

13. Method according to claim 9, further comprising:
    determining a temporal succession of corrected partial stress images ($I\Delta\sigma_k^*$) by multiplying the corrected partial strain image ($I\Delta\varepsilon_k^*$) of index k and the corrected elasticity image ($IE_k^*$) of index k, determining a corrected stress image ($I\sigma_k^*$) by summation of the corrected partial stress images ($I\Delta\sigma_k^*$) having indices between 1 and k inclusive.

14. Method according to claim 13, further comprising:

determining a plurality of corrected stress images ($I\sigma_k^*$), determining a plurality of corrected elasticity images ($IE_k^*$), said corrected stress images and said elasticity images being temporally interlaced, and determining an image of a nonlinearity parameter ($INL_k$), based on the plurality of corrected stress images ($I\varepsilon_k^*$) and the plurality of corrected elasticity images ($IE_k^*$).

15. Method according to claim 14, wherein the value of each pixel of the image of a nonlinearity parameter (INLk) is determined by stress linear regression of pairs of values, the first value of each pair corresponding to the value of a same pixel of a corrected stress image among the plurality and the second value of the pair corresponding to the value of a same pixel of an elasticity image among the plurality, said corrected stress image among the plurality and said corrected elasticity image among the plurality being temporally successive or temporally close, and wherein the stress linear regression is established on the basis of the following relation between stress and elasticity:

$$E = E_0 - \frac{A}{\frac{4}{3} \cdot E_0} \cdot \sigma$$

where

E is the Young's modulus of the pixel of the corrected elasticity image considered, $E_0$ is the Young's modulus of the pixel of the first corrected elasticity image, σ is the stress of the pixel of the corrected strain image considered, and A is the nonlinearity parameter determined for said pixel by said regression.

16. Imaging device comprising an ultrasound probe and a microcomputer which are suitable for implementing the method for ultrasound determination of a corrected image of a medium according to claim 1.

* * * * *